(12) United States Patent
Lunner

(10) Patent No.: US 9,700,261 B2
(45) Date of Patent: Jul. 11, 2017

(54) HEARING ASSISTANCE SYSTEM COMPRISING ELECTRODES FOR PICKING UP BRAIN WAVE SIGNALS

(71) Applicant: Oticon A/S, Smørum (DK)

(72) Inventor: Thomas Lunner, Smørum (DK)

(73) Assignee: OTICON A/S, Smørum (DK)

(*) Notice: Subject to any disclaimer, the term of this patent is extended or adjusted under 35 U.S.C. 154(b) by 4 days.

(21) Appl. No.: 14/860,090

(22) Filed: Sep. 21, 2015

(65) Prior Publication Data

US 2016/0081623 A1   Mar. 24, 2016

(30) Foreign Application Priority Data

Sep. 22, 2014  (EP) .................................... 14185805

(51) Int. Cl.
*H04R 25/00* (2006.01)
*A61B 5/00* (2006.01)
(Continued)

(52) U.S. Cl.
CPC .......... *A61B 5/6817* (2013.01); *A61B 5/0006* (2013.01); *A61B 5/0024* (2013.01);
(Continued)

(58) Field of Classification Search
CPC ... A61B 5/0006; A61B 5/0024; A61B 5/0478; A61B 5/6817; A61B 2560/0468;
(Continued)

(56) References Cited

U.S. PATENT DOCUMENTS 7,206,423 B1 *  4/2007  Feng ................... H04B 13/005
                                                            381/312
7,978,063 B2   7/2011  Baldus et al.
(Continued)

FOREIGN PATENT DOCUMENTS

EP      2 200 342 A1   6/2010
EP      2 581 038 A1   4/2013
(Continued)

OTHER PUBLICATIONS

Cho et al., "The Human Body Characteristics as a Signal Transmission Medium for Intrabody Communication," IEEE Transactions on Microwave Theory and Techniques, vol. 55, No. 5, May 2007, pp. 1080-1086.
(Continued)

*Primary Examiner* — Hemant Patel
(74) *Attorney, Agent, or Firm* — Birch, Stewart, Kolasch & Birch, LLP

(57) ABSTRACT

The application relates to a hearing assistance system comprising first and second spatially separated parts adapted for being mounted fully or partially at a first ear and on the head of a user, respectively, the first and second parts comprising a number of first and second electrodes located at a surface of first and second housings, respectively, to allow said first and second electrodes to contact the skin of the user when said parts are operationally mounted on the user's head. The first and second electrodes are adapted to pick up low-voltage electric signals from the user's brain and a reference voltage, respectively, to provide voltage difference signals. An improved binaural hearing assistance system further comprising a comparison unit for determining the voltage difference signal, and an electric interface allowing the reference voltage or a measure representative thereof to be transferred from said second part to said comparison unit is provided.

20 Claims, 8 Drawing Sheets

(51) Int. Cl.
*G06F 3/01* (2006.01)
*A61B 5/0478* (2006.01)

(52) U.S. Cl.
CPC ............ *A61B 5/0478* (2013.01); *G06F 3/015* (2013.01); *H04R 25/554* (2013.01); *H04R 25/65* (2013.01); *A61B 2560/0468* (2013.01); *H04R 25/552* (2013.01); *H04R 25/70* (2013.01); *H04R 2225/61* (2013.01)

(58) Field of Classification Search
CPC ..... G06F 3/015; H04R 25/552; H04R 25/554; H04R 25/65; H04R 25/70; H04R 2225/61
USPC .................................................. 381/312–331
See application file for complete search history.

(56) References Cited

U.S. PATENT DOCUMENTS

| | | | | |
|---|---|---|---|---|
| 9,025,800 B2* | 5/2015 | Kidmose | ............ | A61B 5/04845 381/312 |
| 2006/0258408 A1* | 11/2006 | Tuomela | ............ | H04B 13/005 455/569.1 |
| 2012/0209101 A1* | 8/2012 | Kidmose | ............ | A61B 5/0478 600/379 |
| 2014/0098981 A1 | 4/2014 | Lunner et al. | | |
| 2015/0272473 A1* | 10/2015 | Zafiroglu | ............... | A61B 5/682 600/302 |

FOREIGN PATENT DOCUMENTS

| | | |
|---|---|---|
| EP | 2 744 224 A1 | 6/2014 |
| WO | WO 2013/026481 A1 | 2/2013 |

OTHER PUBLICATIONS

Lučev et al., "A Capacitive Intrabody Communication Channel from 100 kHz to 100 MHz," Instrumentation and Measurement Technology Conference (I2MTC), IEEE, 2011, 4 pages.

Zimmerman, "Personal Area Networks: Near-field Intrabody Communication," IBM Systems Journal, vol. 35, Nos. 3 & 4, 1996, pp. 609-617.

* cited by examiner

HEARING ASSISTANCE SYSTEM COMPRISING ELECTRODES FOR PICKING UP BRAIN WAVE SIGNALS

TECHNICAL FIELD

The present application relates to a hearing assistance system comprising electrodes for picking up brain wave signals.

BACKGROUND

Hearing instruments comprising electrodes for picking up low-voltage brainwave signals (e.g. EEG signals) are known in the art. The brainwave signals have been proposed for a variety of uses in the hearing aids, e.g. for a modification of the signal processing of a hearing aid in dependence of the brainwave signals.

In case, the brainwave signals are not to be compared and used in the hearing device, where they are picked up, there is a need for a scheme for allowing the transmission of the low-voltage potentials to another device.

SUMMARY

When picking up brain-wave signals (potentials) using in-the-ear encephalogram (EEG) electrodes located on the housing of a single ear piece, the distances between the electrodes are necessarily small (e.g. ≤10 mm). An electric potential created by accumulation of charge on a given electrode (provided by neurons in connection with brain activity) at a given location can be determined from a sum of the contributions of each point charge except for a constant. To be able to compare different brain-wave signals, here termed 'EEG-potentials' $V_{EEGi}$, i=1, 2, . . . , $N_{EEG}$, where $N_{EEG}$ is the number of EEG-potentials (electrodes) at play, each 'EEG-potential' $V_{EEGi}$ is preferably referred to a common reference potential $V_{REF}$, e.g. defined by a reference electrode of the system. To achieve a larger potential difference, $\Delta V_{EEGi} = V_{EEGi} - V_{REF}$, between the active EEG-electrodes ($EEGe_i$) and the reference electrode (REFe, and possibly to reduce or avoid 'cross-talk' between them), the reference electrode is preferably located at a distance from the EEG-electrodes, e.g. larger away than the typical distance between the active EEG-electrodes (e.g. larger than 10 mm, such as larger than 50 mm). According to an embodiment of the present disclosure, the reference electrode is located on a housing of an opposite ear piece with respect to the ear piece where the active EEG electrodes (to be associated with the reference electrode) are located. Thereby, a sufficiently large distance between the active EEG electrodes and the reference electrode is provided. One way or the other, there is, however, a need to communicate one or more electric potentials between two separate parts (e.g. two ear pieces or one ear pieces and another part) to allow the mentioned voltage difference $\Delta V_{EEGi}$ to be determined, so that they can be further processed (and possibly transmitted to another device, e.g. in a conventional way).

The 'brain-wave signals (here also termed 'EEG-signals' or 'EEG-potentials') at a given electrode reflect the variation (over time) in electric potentials resulting from varying ionic currents associated with brain activity. The amplitude variation with time is typically in the 10s of microvolt range e.g. from 10 μV to 100 μV, when the electrodes are attached to the skin (scalp) of the user's head. The variation in time of EEG-signals may comprise oscillations at frequencies in the Hz range, e.g. in the range from 1 Hz to 20 Hz, such as between 5 Hz and 10 Hz.

A hearing device is a portable device of small size, e.g. energized by a battery. The hearing device therefore has a limited power budget (due to a relatively small battery capacity). Hence, there is a restriction of the allocation of power to any given task of a hearing device. Wireless transceivers are one of the relatively large power consumers of a modern hearing device. Wireless technologies for use in hearing devices are thus carefully selected, e.g. to optimize their power consumption to bandwidth ratio. The use of ear-to-ear (e2e) communication between two hearing devices is generally limited (in time and/or bandwidth) for this reason.

An object of the present application is to provide an improved hearing assistance system.

Objects of the application are achieved by the invention described in the accompanying claims and as described in the following.

A Hearing Assistance System:

In an aspect of the present application, an object of the application is achieved by a hearing assistance system comprising
  a first part adapted for being mounted fully or partially at a first ear or in an ear canal of the first ear of a user, the first part comprising
    a first housing,
    a number of first electrodes located at a surface of said first housing to allow said first electrodes to contact the skin of the user when said first part is operationally mounted on the user, each of the first electrodes being adapted to pick up a low-voltage electric signal from the user's brain,
  a second part adapted for being mounted on the body spatially separated from said first part, the second part comprising
    a number of second electrodes arranged to allow said second electrodes to contact the skin of the user when second said part is operationally mounted on the user.

At least one of the second electrodes of the second part being configured as a reference electrode and adapted to pick up a reference voltage intended to constitute a reference voltage for the low-voltage electric signal(s) from the user's brain picked up by the first electrodes thereby allowing a voltage difference signal to be determined for each of said first electrodes The hearing assistance system comprises a comparison unit for determining said voltage difference signal(s), and an electric interface allowing said reference voltage or a measure representative thereof to be transferred from said second part to said comparison unit.

This has the advantage of providing a hearing assistance system with improved capability of measuring and processing brainwave signals.

Embodiments of the present disclosure provides EEG-potentials related to nerve responses from a user's brain. The EEG potentials are e.g. picked up by an ear piece comprising electrodes located at or in an ear of the user. A reference potential from an electrode located elsewhere on the user's body (e.g. from another ear piece located in or at the user's other ear) is further provided. An electric interface availing the EEG-potentials and the reference potential in the same device (e.g. an ear piece or another device) is provided whereby the EEG-signals can be provided as voltage differences. This has the advantage of enabling a location of a reference electrode a distance away from EEG-electrodes AND to facilitate that potentials picked up by the EEG and reference electrodes can be compared in the same device (to refer the EEG potentials to the reference potential, thus providing individual EEG-voltage differences that can be processed and transmitted).

Preferably, the second part is configured to be mounted on the head, e.g. fully or partially at a second ear or in an ear canal of the second ear of the user.

In an embodiment, the second part comprises a housing. In an embodiment, the second electrodes are located at (or movable to) a surface of the second housing to allow the second electrodes to contact the skin of the user when the second part is operationally mounted on the user.

In an embodiment, the hearing assistance system comprises a listening device, e.g. a hearing device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

In an embodiment (or an alternative aspect), the first part may be adapted for being partially implanted in the head (e.g. in or near cochlea) at a first (and/or second) ear of a user. In an embodiment, an implanted electrode may be alternatively or additionally used to pick up a low-voltage electric signal from the user's brain. In an embodiment, an implanted electrode may be used as a reference electrode for referencing low-voltage electric signal from the user's brain to provide the brainwave voltage difference signals.

In an embodiment, the hearing assistance system, e.g. a hearing device of the system, is adapted to provide a frequency dependent gain and/or a level dependent compression and/or a transposition (with or without frequency compression) of one or more frequency ranges to one or more other frequency ranges, e.g. to compensate for a hearing impairment of a user. In an embodiment, the hearing device comprises a signal processing unit for enhancing an electric input signal representative of sound and providing a processed electric output signal.

In an embodiment, the hearing assistance system, e.g. a hearing device of the system, comprises an output unit for providing a stimulus perceived by the user as an acoustic signal based on a processed electric signal. In an embodiment, the output unit comprises a number of electrodes of a cochlear implant or a vibrator of a bone conducting hearing device. In an embodiment, the output unit comprises a receiver (speaker) for providing the stimulus as an acoustic signal to the user.

In an embodiment, the hearing assistance system, e.g. a hearing device of the system, comprises an input unit for providing an electric input signal. In an embodiment, the hearing assistance system comprises a beamformer adapted to enhance a target acoustic source among a multitude of acoustic sources in the local environment of the user wearing the hearing assistance system.

In an embodiment, the electric interface comprises a galvanic connection, e.g. comprising one or more electric conductors. In an embodiment, the reference voltage (an analogue potential) of the reference electrode is transferred to the comparison unit via an electric conductor between said second part and said comparison unit. In an embodiment, the galvanic connection is established by transmission of an alternating current via the user's skin from a transmitting to a receiving electrode.

In an embodiment, the electric interface comprises a wireless link. In an embodiment, each of the first and second parts comprises a transceiver unit configured to establish a (e.g. digital) communication link to another part of the hearing assistance system allowing reception and/or transmission of data. In an embodiment, the transceiver units comprise appropriate modulation and demodulation circuitry to transform signals picked up by the first and/or second electrodes to/from a frequency range adapted to the communication link (e.g. in a frequency band in the MHz or GHz range). In an embodiment, the system is configured to operate in a part of the frequency range between 100 kHz and 70 GHz, e.g. in the range around 2.4 GHz or below 1 GHz. In an embodiment, each of the first and second parts comprise first and second common voltages, respectively, to which the brainwave signals picked up by the first and second electrodes, respectively, are referred. In an embodiment, the brainwave signals picked up by the first and/or second electrodes typically have amplitudes in the range from 10 μV to 100 μV, and frequencies in the range from 1 Hz to 20 Hz.

In an embodiment, the hearing assistance system, e.g. a transceiver unit, comprises an amplifier unit operationally connected to at least one of the first or second electrode(s) and adapted for amplifying said low voltage electric signal(s) or said reference voltage to provide amplified brain signal(s). In an embodiment, said amplifier unit is connected to a common ground of the part of the hearing assistance system, where it is located. In an embodiment, a transceiver unit comprises a transmitter unit configured to transmit a (possibly amplified) low-voltage electric signal. In an embodiment, a transceiver unit comprises a receiver unit configured to receive a low-voltage electric signal.

In an embodiment, the electric interface comprises a wireless link based on radiated fields. In an embodiment, the wireless link is based on a digital standardized scheme, e.g. Bluetooth (e.g. Bluetooth low energy) or similar technology suitable for portable devices, and having relatively low power consumption (and providing relatively low transmission range). In an embodiment, the wireless link is configured to operate in the GHz range.

In an embodiment, the wireless link is based on near-field coupling, e.g. a link based on near-field communication, e.g. a capacitive or an inductive link. In an embodiment, the wireless link is configured to operate in the MHz range.

A certain application of capacitive human body transmission is the use in hearing aids and ear-to-ear communication. Thus, audio range transmission would be possible to transfer e.g. from one ear piece to another, via an intermediate (e.g. remote control) device, as e.g. described in U.S. Pat. No. 7,206,423. U.S. Pat. No. 7,206,423 deals with the use of intra-body communication in a hearing aid. An audio signal picked up by a microphone of a hearing aid (and possibly further processed) is transmitted to another device worn by the user via the skin of the user.

In an embodiment of the present invention, it is proposed to transmit EEG signals between the ears (or between devices located at the respective ears of the user, and possibly involving a third intermediate device).

In an embodiment, the electric interface comprises a body-network. The human body itself may act as a signal transmission medium (cf. e.g. [Zimmerman; 1996], [Cho et al.; 2007]; [Lucev et al.; 2011]). The benefits of body transmission is low power consumption and high bandwidth, and the connection is always available. For many applications related to hearing devices, the short transmission range (2 m=the approximate distance between the arms) is acceptable. The body capacity transmission require a number of electrodes, cf. e.g. FIG. 5.

A reference potential ($V_{REF}$) is advantageously transferred, e.g. from the second to the first part (and/or to another 'auxiliary device', e.g. a processing or relaying part located on or near the user's body, cf. e.g. FIG. 2) thereby enabling the brainwave (or EEG) signals to be referred to the reference potential $V_{REF}$. The EEG signals are potentials $V_{EEGi}$, i=1, 2, ... $N_{elec}$, picked up by a number $N_{elec}$ of electrodes. A further processing of the voltage differences $\Delta V_{EEGi} = V_{EEGi} - N_{REF}$, i=1, 2, $N_{elec}$, can then be performed in the first part (cf. e.g. FIG. 1), or $\Delta V_{EEGi}$ can be transmitted to a dedicated 'processing part', e.g. via a conventional (e.g. wireless) communication link (cf. e.g. processing unit PRO in FIG. 2).

In an embodiment, (each of) the first and second parts of the hearing assistance system comprise one of a Tx- and Rx-ground electrodes exhibiting substantially equal virtual Tx- and Rx-ground potentials established via a capacitive coupling to an external ground (e.g. earth ground), at least partly via the user's body (cf. FIG. 1B or FIG. 5).

In an embodiment, the first and/or second part comprises an analogue to digital (AD) converter to digitize (and possibly amplify) a voltage difference signal ($\Delta V_{EEGi}$). In an embodiment, the voltage difference ($\Delta V_{EEGi}$) is digitized (and possibly amplified) before being transmitted to another device (e.g. via a wireless link).

In an embodiment, the hearing assistance system, e.g. a hearing device of the system, comprises an antenna and transceiver circuitry for wirelessly receiving or transmitting a direct electric input signal from another device. In an embodiment, the hearing assistance system comprises a (possibly standardized) electric interface (e.g. in the form of a connector) for receiving a wired direct electric input signal from another device. In an embodiment, the direct electric input signal represents or comprises an audio signal and/or a control signal and/or an information signal (e.g. a brainwave signal or a signal derived therefrom). In an embodiment, the hearing assistance system comprises modulation/demodulation circuitry for modulating/demodulating the transmitted/received signal. In general, the wireless link established by a transmitter and antenna and transceiver circuitry of the hearing assistance system can be of any type. In an embodiment, the wireless link is used under power constraints, e.g. in that the hearing assistance system comprises a portable (typically battery driven) device. In an embodiment, the wireless link is a link based on near-field communication, e.g. based on capacitive or an inductive coupling between antenna elements of transmitter and receiver parts. In another embodiment, the wireless link is based on far-field, electromagnetic radiation. In an embodiment, the communication via the wireless link is arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying), MSK (minimum shift keying), or QAM (quadrature amplitude modulation).

In an embodiment, the communication between the hearing assistance system and other devices is in the base band (audio frequency range, e.g. between 0 and 20 kHz). Preferably, communication between the hearing assistance system and the other device is based on some sort of modulation at frequencies above 100 kHz. Preferably, frequencies used to establish a communication link between the hearing assistance system and other devices is below 70 GHz, e.g. located in a range from 50 MHz to 50 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology).

In an embodiment, the hearing assistance system, e.g. a hearing device of the system, comprises a forward or signal path between an input transducer (microphone system and/or direct electric input (e.g. a wireless receiver)) and an output transducer. In an embodiment, the signal processing unit is located in the forward path. In an embodiment, the signal processing unit is adapted to provide a frequency dependent gain according to a user's particular needs. In an embodiment, the hearing device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, the hearing assistance system, e.g. a hearing device of the system, comprise an analogue-to-digital (AD) converter to digitize an analogue input (e.g a microphone input signal or a brainwave signal) with a predefined sampling rate, e.g. 20 kHz. In an embodiment, the hearing devices comprise a digital-to-analogue (DA) converter to convert a digital signal to an analogue output signal, e.g. for being presented to a user via an output transducer.

In an embodiment, the hearing assistance system, e.g. a hearing device of the system, e.g. an input unit, and/or a transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing device from a minimum frequency $f_{min}$ to a maximum frequency $f_{max}$ comprises a part of the typical human audible frequency range from 20 Hz to 20 kHz, e.g. a part of the range from 20 Hz to 12 kHz.

In an embodiment, the hearing assistance system, e.g. a hearing device of the system, further comprises other relevant functionality for the application in question, e.g. compression, noise reduction, feedback suppression, etc.

In an embodiment, the number of second electrodes is smaller than or equal to five, such as smaller than three. In an embodiment, the number of second electrodes is one. In an embodiment, the second part only comprises one electrode, namely the reference electrode. In an embodiment, the reference electrode is substantially identical to an EEG-electrode. In an embodiment, the reference electrode has a larger area of contact than an EEG-electrode. The electrodes are configured to have a contact with the skin of the user when operationally mounted, and to thereby establish an electrical contact to the skin.

In an embodiment, the hearing assistance system is configured to maximize the area of contact of the reference electrode with the skin. Such optimization of the area of contact is preferably performed within the size constraints imposed by the part (and possible other electrodes on the part) where the reference electrode is located. In an embodiment, the form of a housing and/or the location of the electrode(s) on the housing is/are optimized to maximize the contact between the electrode(s) and the skin.

In an embodiment, the first part is implemented as an ear piece (e.g. formed as or comprising an ear mould) adapted for being located in or at the left and right ear or ear canals of the user. In an embodiment, the first part form part of a first hearing device of the hearing assistance system. In an embodiment, the second part is configured to be located on the head of the user other than in an ear canal, e.g. at the scalp of the user.

In an embodiment, the second part is adapted for being mounted fully or partially at a second ear or in an ear canal of the second ear of the user. In an embodiment, each of the first and second parts comprises a number of first and second EEG electrodes and a first and second reference electrode, respectively. In an embodiment, the first and second parts are implemented as ear pieces (e.g. ear moulds) adapted for being located in or at the left and right ear or ear canals of the user. In an embodiment, the first and second parts comprise the same number of EEG and reference electrodes. In an embodiment, the reference voltage ($V_{REF2}$) picked up by the reference electrode of the second part is used as a reference voltage for the EEG potentials ($V_{EEGi}$) picked up by the EEG electrodes of the first part, and vice versa. In an embodiment, the first and second parts form part of first and second hearing devices of the hearing assistance system, e.g. providing a binaural hearing assistance system. In an embodiment, each of the first and second parts comprise 2-5 EEG electrodes and one reference electrode. In an embodiment, the second ear piece only comprises one electrode, the reference electrode. In an embodiment, the reference electrode is adapted to have a substantially circumferential layout around the second ear piece.

In an embodiment, the first part comprises the comparison unit. In an embodiment, the comparison part form part of a third part, e.g. an auxiliary device, e.g. a remote control, or other processing part, e.g. a communication device, such as a SmartPhone. In an embodiment, the second part comprises a second comparison unit. In an embodiment, separate sets of EEG-potential differences are generated in the first and second parts. In an embodiment, one common set of EEG-potential differences are generated in the first and second parts, e.g. in that the EEG-potential differences generated in one part is communicated to the other part via a communication link, e.g. a wireless link.

In a further aspect, a hearing assistance system as described above, in the 'detailed description of embodiments' and in the claims, the hearing assistance system comprising a hearing device AND an auxiliary device is moreover provided.

In an embodiment, the system is adapted to establish a communication link between the hearing device(s) and the auxiliary device to provide that information (e.g. control and status signals (including EEG-signals), possibly audio signals) can be exchanged or forwarded from one to the other.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing device. In an embodiment, the auxiliary device is or comprises a communication device, e.g. a cellular telephone, such as a SmartPhone or an equivalent device. In an embodiment, the auxiliary device is or comprises a user interface (e.g. in the form of a remote control) for controlling functionality and operation of the hearing device(s). In an embodiment, the function of the user interface/remote control is implemented in a SmartPhone, the SmartPhone possibly running an APP allowing to control the functionality of the audio processing device via the SmartPhone (the hearing device(s) comprising an appropriate wireless interface to the SmartPhone, e.g. based on Bluetooth or some other standardized or proprietary scheme). In an embodiment, the remote control is configured to perform processing related to the captured EEG-signals.

In the present context, a SmartPhone, may comprise
(A) a cellular telephone comprising a microphone, a speaker, and a (wireless) interface to the public switched telephone network (PSTN) COMBINED with
(B) a personal computer comprising a processor, a memory, an operative system (OS), a user interface (e.g. a keyboard and display, e.g. integrated in a touch sensitive display) and a wireless data interface (including a Web-browser), allowing a user to download and execute application programs (APPs) implementing specific functional features (e.g. displaying information retrieved from the Internet, remotely controlling another device, combining information from various sensors of the SmartPhone (e.g. camera, scanner, GPS, microphone, etc.) and/or external sensors to provide special features, etc.).

In an aspect, a hearing assistance system is provided. The hearing assistance system comprises
a first part comprising a first hearing device, e.g. a hearing aid, adapted for being mounted fully or partially at a first ear or in an ear canal of the first ear of a user, the first hearing device comprising
a first housing,
a number of first electrodes located at a surface of said first housing to allow said first electrodes to contact the skin of the user when said first part is operationally mounted on the user, each of the first electrodes being adapted to pick up a low-voltage electric signal from the user's brain,
a second part, e.g. comprising a hearing device, adapted for being mounted on the body spatially separated from said first part, the second part comprising
a number of second electrodes arranged to allow said second electrodes to contact the skin of the user when second said part is operationally mounted on the user,
at least one of the second electrodes of the second part being configured as a reference electrode and adapted to pick up a reference voltage intended to constitute a reference voltage for the low-voltage electric signal(s) from the user's brain picked up by the first electrodes,
wherein the hearing assistance system further comprises
a comparison unit for determining and/or processing voltage difference signal(s), and
an electric interface allowing said reference voltage or a measure representative thereof to be transferred from said second part to said comparison unit, thereby allowing a voltage difference signal to be determined and/or processed for each of said first electrodes.

Use:

In an aspect, use of a hearing device as described above, in the 'detailed description of embodiments' and in the claims, is moreover provided.

Definitions:

In the present context, a 'hearing device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing device may comprise a single unit or several units communicating electronically with each other.

More generally, a hearing device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing devices, an amplifier may constitute the signal processing circuit. In some hearing devices, the output means may comprise an output transducer, such as e.g. a loudspeaker for providing an air-borne acoustic signal or a vibrator for providing a structure-borne or liquid-borne acoustic signal. In some hearing devices, the output means may comprise one or more output electrodes for providing electric signals.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing assistance system' refers to a system comprising one or two hearing devices, and a 'binaural hearing assistance system' refers to a system comprising one or two hearing devices and being adapted to cooperatively provide audible signals to both of the user's ears. Hearing assistance systems or binaural hearing assistance systems may further comprise 'auxiliary devices', which communicate with the hearing devices and affect and/or benefit from the function of the hearing devices. Auxiliary devices may be e.g. remote controls, audio gateway devices, mobile phones, public-address systems, car audio systems or music players. Hearing devices, hearing assistance systems or binaural hearing assistance systems may e.g. be used for compensating for a hearing-impaired person's loss of hearing capability, augmenting or protecting a normal-hearing person's hearing capability and/or conveying electronic audio signals to a person.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out. Throughout, the same reference signs are used for identical or corresponding parts.

Figure 1A:
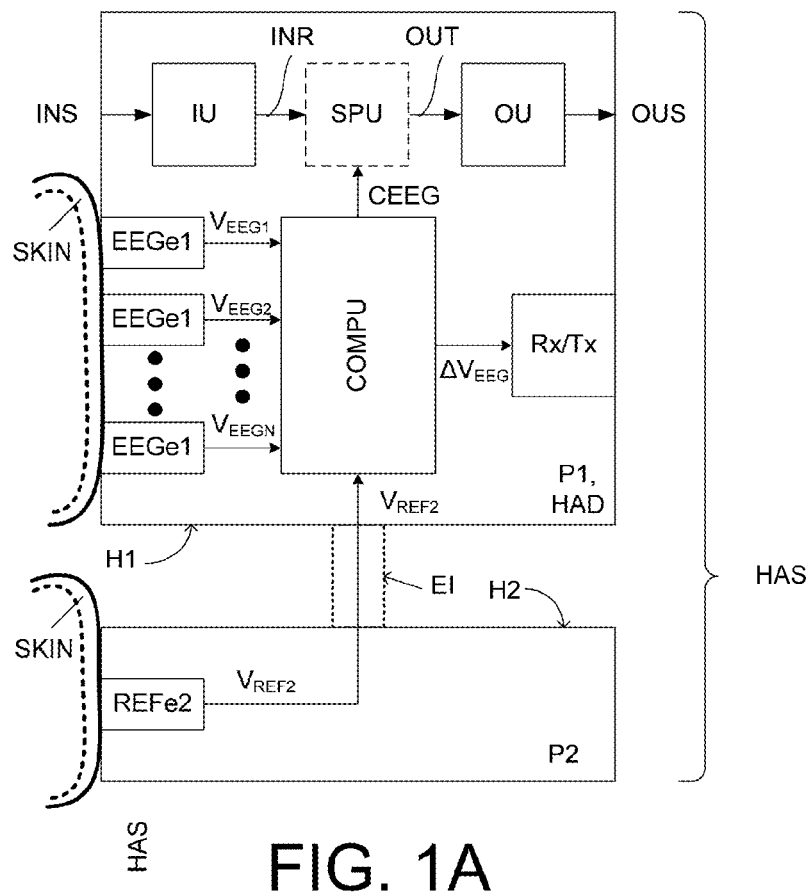
FIG. 1 shows first (FIG. 1A) and second (FIG. 1B) embodiments of a hearing assistance system configured for picking up brainwave (e.g. EEG) signals from a user's brain, and comprising first and second parts adapted for being mounted on the head of the user.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Embodiments of the present application relates to hearing assistance systems e.g. comprising two hearing assistances devices configured to enable communication between the two devices (termed ear-to-ear communication, in the present disclosure). Embodiments of the present application further relates to the recording of brainwave signals using electrodes forming part of at least one of the hearing devices. Embodiments of the disclosure relates specifically to a hearing assistance system comprising a reference electrode for capturing a reference voltage, and to the expression of the brainwave signals as potential differences relative to the reference voltage. In an aspect, the application relates to the use of a hearing assistance system.

Embodiments of the disclosure may e.g. be useful in applications such as binaural hearing assistance systems.

The present disclosure deals with the use of a body worn communication system to pick up brainwave (EEG) signals from a user's brain and in particular with the communication of an electric field potential from one part of the system (e.g. from one body worn device) to another. Thereby the problem of creating a remote reference voltage $V_{REF}$ for EEG signals is addressed. One way of addressing the problem is to establish a galvanic contact between the locations/devices where the respective EEG and reference electrodes are located (cf. e.g. FIG. 1A). Otherwise, a voltage difference $\Delta V_{REF}$ is needed to be able to electrically transfer the reference voltage $V_{REF}$ from one location to another, e.g. via a (wireless) communication link, see e.g. FIG. 1B). In a preferred embodiment, EEG-electrodes (EEGe) are located in a first hearing device positioned at a first ear and a corresponding reference electrode (REFe) is located in a second hearing device positioned at a second ear (cf. e.g. FIG. 4). Thereby a relatively large distance between the active EEG-electrodes and the reference electrode can be provided. In an embodiment, a virtual ground ($V_{VT-GND}$) created via the user's body and the surrounding 'earth' is used as reference (ground) for the reference voltage $V_{REF}$ (cf. so-called body-networks, cf. e.g. FIG. 5, e.g. $Tx_{GND}$ ($Ext_{GND}$) in FIG. 5B). Thereby, a reference voltage difference $\Delta V_{REF} = V_{REF} - V_{VT-GND}$ (cf. e.g. $V_{REF2} - Tx_{GND}$ in FIG. 5B) can be transmitted to another device using a conventional (e.g. wireless) communication link (or alternatively, via the skin of the body), cf. e.g. dashed arrows denoted $\Delta V_{REF1}$ and $\Delta V_{REF2}$, respectively, between the two hearing devices in FIG. 4. In the receiving device, a virtual ground can similarly be established (cf. e.g. $Rx_{GND}$ ($Ext_{GND}$) in FIG. 5B), whereby the original reference voltage $V_{REF}$ can be determined ($V_{REF} = \Delta V_{REF} + V_{W-GND}$) for use with the EEG-voltages $V_{EEGi}$. The EEG-voltages $V_{EEGi}$ can then be referred to EEG-reference voltages $V_{REF}$ (providing voltage difference signals $\Delta V_{EEGi} = V_{EEGi} - V_{REF}$, i=1, 2, . . . , N, where N is the number of EEG-electrodes) and subsequently be processed and/or transmitted to another device(s), cf. e.g. dashed arrows denoted $\Delta V_{EEG1i}$ and $\Delta V_{EEG2i}$, respectively, between the two hearing devices. Thereby larger EEG-(difference) signals can be provided compared to a situation where EEG and reference electrodes are located in the same device (e.g. a hearing device).

Figure 1B:
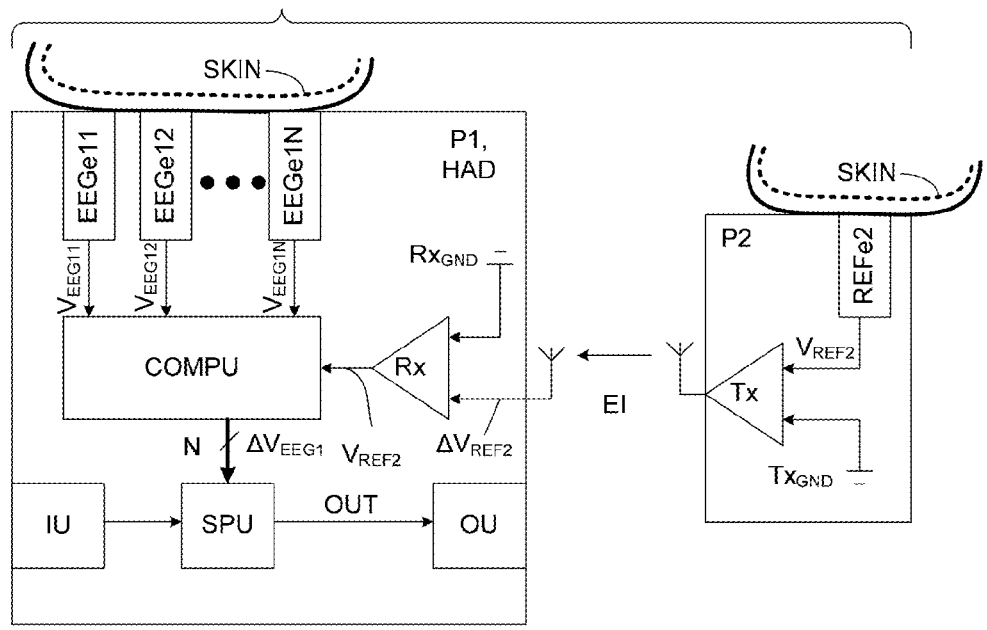

FIG. 1 shows first (FIG. 1A) and second (FIG. 1B) embodiments of a hearing assistance system configured for picking up brainwave (e.g. EEG) signals from a user's brain, and comprising first and second parts adapted for being mounted on the head of the user.

FIG. 1A shows an embodiment of a hearing assistance system (HAS) comprising a first part (P1) adapted for being mounted at an ear of a user and a second part (P2) adapted for being mounted on the head of the user spatially separated from the first part. The first part (P1) comprises a first housing (H1), and a number of first electrodes (EEGe1) located at or accessible from a surface of the first housing (H1) to allow the first electrodes to contact the skin (SKIN) of the user when the first part is operationally mounted at the ear of the user. Each of the first electrodes (EEGe1) are adapted to pick up a low-voltage electric signal (EEG-signal) from the user's brain ($V_{EEG1}$, $V_{EEG2}$, . . . , $V_{EEGN}$, where N is the number of EEG-electrodes). The second part (P2) comprises a second housing (H2), and a number of second electrodes (here one electrode, a reference electrode (REFe2), is shown) located at or accessible from a surface of the second housing to allow the second electrodes to contact the skin (SKIN) of the user when the second part is operationally mounted on the head of the user. Alternatively, the second electrode(s) is/are (an) independent electrode(s), which is not mounted on a second housing. In an embodiment, the second part (P2) does not comprises a (second) housing (H2). At least one of the second electrodes (REFe2) is configured as a reference electrode and adapted to pick up a reference voltage $V_{REF2}$ intended to constitute a reference voltage for the low-voltage electric signal(s) from the user's brain (EEG-signal) picked up by the first electrodes (EEGe1) thereby allowing a voltage difference signal $\Delta V_{EEGi}$ to be determined for each of the EEG-signals picked up by the (N) first electrodes. The determination of voltage difference signals $\Delta V_{EEGi}$ is performed in a comparison unit (COMPU), here shown to be located in the first part (P1). The hearing assistance system (HAS) further comprises an electric interface (EI) allowing the reference voltage $V_{REF2}$ or a measure representative thereof to be transferred from the second part (P2) to the comparison unit (COMPU) located in the first part (P1). In the embodiment of FIG. 1A, the electric interface (EI) comprises a galvanic connection between the first and second parts, electrically connecting the reference electrode (REFe2) to the comparison unit (COMPU). Thereby the EEG-signals from the user's brain ($V_{EEG1}, V_{EEG2}, \ldots, V_{EEGN}$) can be directly compared to the reference voltage $V_{REF2}$. The electrical conductor providing the galvanic connection may be an isolated wire located at the surface of the head of the user (e.g. hidden in the hair of the user) or be fully or partially buried under the skin of the user's head. The comparison unit (COMPU) (or the signal processing unit SPU) may perform further processing of the reference voltage and/or of the EEG signals (voltages or voltage differences). A time average (e.g. an accumulated time average) of the reference voltage may e.g. be performed by the comparison unit (COMPU) before being used to calculate the EEG-voltage differences.

The first part (P1) form part of (e.g. integrated with or connected to) a hearing device (HAD). The hearing device (HAD) comprises a forward path for propagating a signal representing sound from an input unit (IU) to an output unit (OU). The hearing device comprises an input unit (IU) for providing an electric input signal INR based on an input signal INS representing sound. The input unit (IU) may comprise an input transducer, e.g. a microphone or an accelerometer or other vibration sensor. The hearing device (e.g. the forward path) comprises a signal processing unit (SPU), e.g. adapted to provide a frequency dependent gain to compensate for a hearing loss of a user, and/or to otherwise enhance the input signal INR and provide a processed output signal OUT. The hearing device further comprises an output unit (OU) for providing a stimulus OUS perceived by the user as an acoustic signal based on a processed electric signal (OUT). In an embodiment, the output unit comprises a number of electrodes of a cochlear implant or a vibrator of a bone conducting hearing device. In an embodiment, the output unit comprises a receiver (speaker) for providing the stimulus as an acoustic signal to the user.

The signal processing unit (SPU) is configured to process the electric input signal INR depending on a number of processing algorithms and to provide a resulting processed signal OUT. One or more of the signal processing algorithms are parameterized and parameters controllable in dependence on detectors or analysis of properties of the present environment of the user and/or of the present condition of the user. For example (as illustrated in FIG. 1), the processing performed by the signal processing unit (SPU) may be influenced by the resulting EEG measurements (e.g. based on voltage difference signal $\Delta V_{EEGi}$ or data derived therefrom, possibly combined with other parameters or properties). This is illustrated in FIG. 1A by control signal CEEG from the comparison unit (COMPU) to the signal processing unit (SPU).

FIG. 1B shows an embodiment of a hearing assistance system (HAS) as described in connection with FIG. 1A, but where the electric interface (EI) comprises a wireless link instead of a galvanic connection for the transfer of the reference voltage from the second part (P2) to the first part (P1). The wireless link comprises antenna and transceiver circuitry in the transmitting (P2) and receiving (P1) parts, respectively, allowing the transmission of a voltage difference $\Delta V_{REF2}$ from the second (P2) to the first part (P1). In the second part a transmitter ground $V(Tx_{GND})$ is used as reference for the reference voltage $V_{REF2}$ provided by reference electrode RFEe2. The two voltages are fed to wireless transmitter unit Tx, e.g. comprising an analogue to digital (AD) converter and/or appropriate modulation/coding circuitry. In an embodiment, the antenna and transceiver circuitry is adapted to establish a digital link, e.g. according to Bluetooth (e.g. Bluetooth Low Energy) or other low power wireless transmission technology (e.g. ZigBee). In an embodiment, the wireless link is based on near-field communication, e.g. based on capacitive or inductive coupling between corresponding antenna elements in the first and second parts of the hearing assistance system. The first part (P1) forming part of a hearing device (HAD) comprises antenna and transceiver circuitry allowing the reception of the voltage difference $\Delta V_{REF2}$ from the second part (P2). The transceiver of the first part (P1) comprises wireless receiver Rx, e.g. comprising a low-noise amplifier and/or demodulation/decoding circuitry to extract voltage difference $\Delta V_{REF2}$ and to provide reference voltage $V_{REF2}$ by addition of receiver ground $V(Rx_{GND})$. In the embodiment of FIG. 1B, the resulting EEG-signal voltage differences $\Delta V_{EEGi}$ are forwarded from the comparison unit (COMPU) to the signal processing unit (SPU) for further processing and/or as inputs to the control of a processing algorithm (cf. control signal CEEG In FIG. 1A)

Figure 2A:
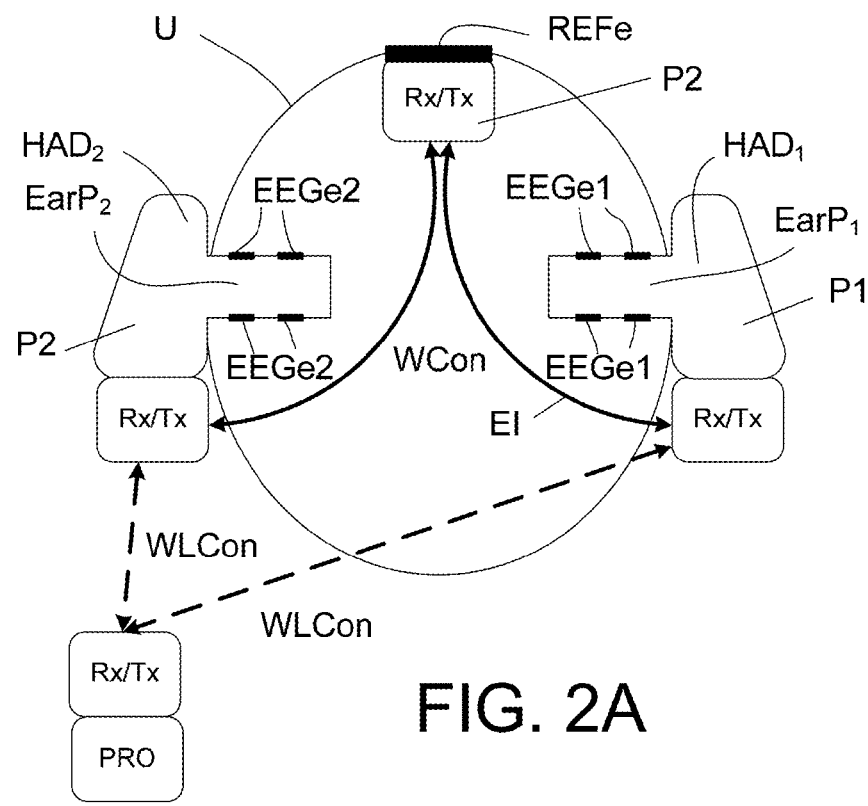
FIG. 2 shows use scenarios of first (FIG. 2A), second (FIG. 2B) and third (FIG. 2C) embodiments of a hearing assistance system comprising EEG and reference electrodes according to the present disclosure.
Figure 2B:
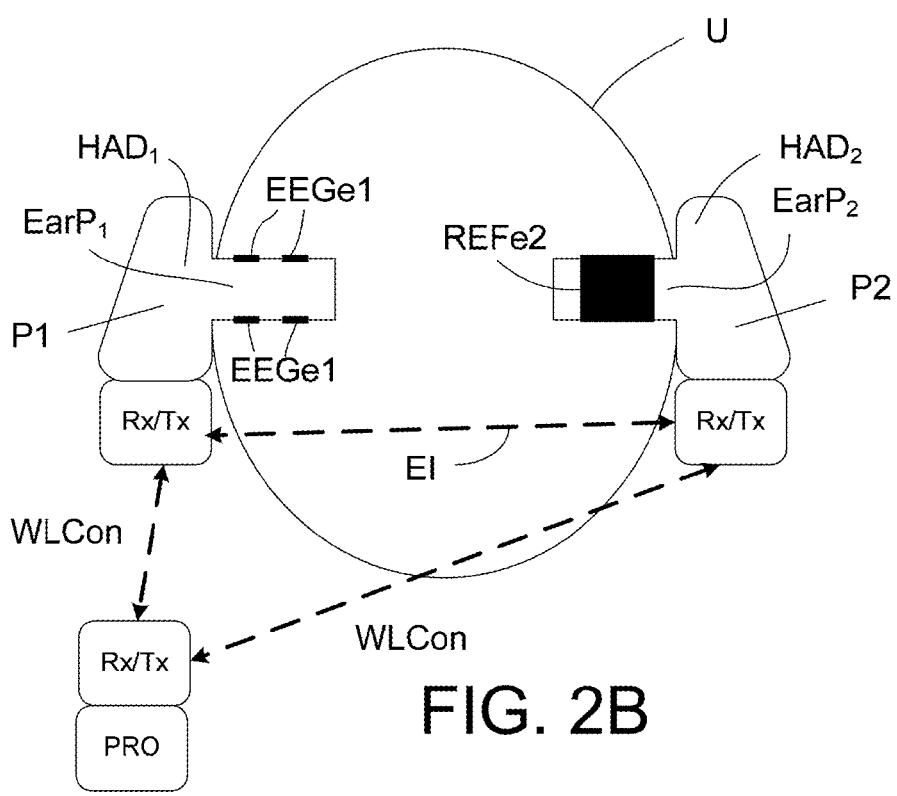
Figure 2C:
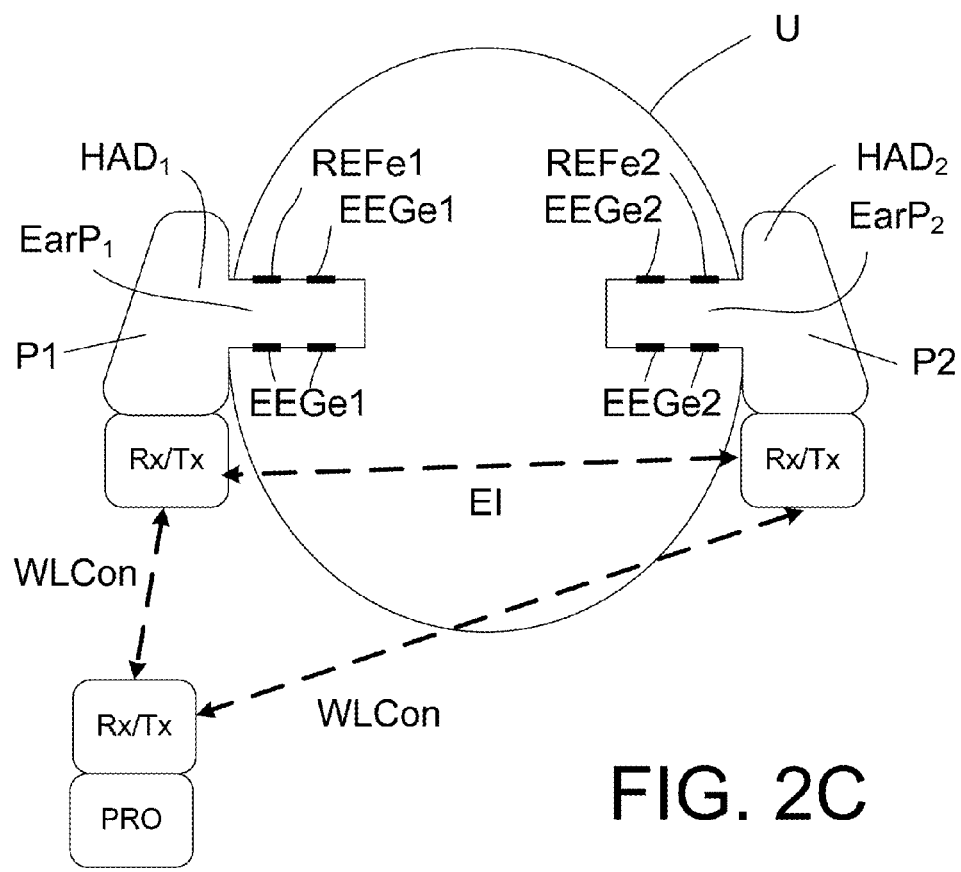

FIG. 2 shows use scenarios of first (FIG. 2A), second (FIG. 2B) and third (FIG. 2C) embodiments of a hearing assistance system comprising EEG and reference electrodes according to the present disclosure. FIG. 2 illustrates embodiments of a hearing assistance system comprising first and second hearing devices ($HAD_1$, $HAD_2$) mounted at or in the respective ears of a user (U). The first and second hearing devices ($HAD_1$, $HAD_2$) each comprises first and second ear pieces ($EarP_1$, $EarP_2$) (constituting or forming part of parts P1, P2), respectively, each being adapted to be located at the ear, fully or partially in the ear canal, and each comprising a number of first and second electrodes (EEGe1, EEGe2), respectively. When the first and second hearing devices are operationally mounted on the user, the electrodes of the ear pieces are positioned to have electrical contact with the skin of the user to enable the sensing of brainwave signals. The hearing assistance system further comprises an optional auxiliary device (PRO), e.g. for processing EEG-signals (and optionally performing other processing tasks related to the hearing assistance system) and/or providing a user interface for the hearing assistance system. Each of the first and second hearing devices ($HAD_1$, $HAD_2$) and the auxiliary device (PRO) comprises antenna and transceiver circuitry (Rx/Tx) configured to establish a wireless link (WL-Con) to each other.

The embodiment of FIG. 2A comprises a specific second part (P2) comprising a reference electrode (REFe) and an electric interface (EI) providing a galvanic connection to a first part (P1) forming part of the first hearing device (HAD$_1$). The reference electrode of the second part is e.g. located in the scalp of the user (U), e.g. substantially in a symmetry point between the left and right ears of the user. The respective transceiver units (Rx/Tx) comprise appropriate connection of a conductor from the reference electrode (REFe) of the second part (P2) to the comparison (COMPU, see FIG. 1) of the first part (P1). In the embodiment of FIG. 2A, the electric interface (EI) also provides a galvanic (wired) connection WCon between the second part (P2) and the second hearing device (HAD$_2$). Thereby, EEG signals in both of the first and second hearing devices (HAD$_1$, HAD$_2$) can be referenced to the same reference voltage V$_{REF}$, and the resulting EEG voltage difference signals can be transmitted to another device (e.g. auxiliary device PRO) and/or exchanged between the first and second hearing devices (HAD$_1$, HAD$_2$), either directly or via the auxiliary device (e.g. using wireless links WLCon).

In the embodiment of FIG. 2B, the first and second hearing devices (HAD$_1$, HAD$_2$) comprises first and second parts (P1, P2). The first hearing device (HAD$_1$) comprises EEG-electrodes (EEGe1, e.g. four) arranged around the outer surface of the ear piece (EarP1), e.g. to separate the EEG-electrodes maximally from each other, while ensuring good electrical contact to the skin of the user when mounted. The second hearing device (HAD$_2$) comprises reference-electrode (REFe2) located along the periphery of the ear piece (EarP$_2$). The ear piece (EarP$_2$) and the reference electrode is preferably configured to maximize the area of contact of the reference electrode (REFe2) with the skin. The reference voltage V$_{REF}$ picked up by reference electrode (REFe2) may e.g. be communicated to the first hearing device (HAD$_1$) via electric interface (EI), e.g. comprising a wireless link, e.g. an analogue or digital wireless link, and/or to the auxiliary device (PRO), e.g. via one or more wireless links (WLCon), as mentioned above, e.g. in connection with FIG. 1B. Alternatively, the electric interface (EI) may comprise a galvanic connection between the first and second hearing devices (HAD$_1$, HAD$_2$) as discussed in connection with FIGS. 1A and 2A. Further alternatively, the reference voltage V$_{REF}$ picked up by reference electrode (REFe2) may be communicated to the first hearing device (HAD$_1$), and/or to the auxiliary device (PRO), using body communication, as discussed in connection with FIG. 5.

In the embodiment of FIG. 2C, the first and second hearing devices (HAD$_1$, HAD$_2$) comprises first and second parts (P1, P2), respectively. Further, the first hearing devices (HAD$_1$, HAD$_2$) each comprises EEG-electrodes (EEGe1, EEGe2) and a reference electrode (REFe1, REFe2), respectively, arranged on the outer surface of the respective ear pieces (EarP1, EarP$_2$). Each of the first and second parts (P1, P2) comprises a number of EEG-electrodes (EEGe1, EEGe2), here 3 are shown (but more or less may be present in practice depending on the application), and a reference electrode (REFe1, REFe2). Thereby the reference voltage (V$_{REF2}$) picked up by the reference electrode (REFe2) of the second part (P2) can be used as a reference voltage for the EEG potentials (V$_{EEG1i}$) picked up by the EEG electrodes (EEGe1) of the first part (P1), and vice versa. In an embodiment, the first and second hearing devices provides a binaural hearing assistance system. The reference voltages (V$_{REF1}$, V$_{REF2}$) may be transmitted from one part to the other (P1<->P2) via electric interface EI (and optionally auxiliary device PRO) as discussed in connection with FIG. 2A, 2B and FIG. 1A, 1B. The two sets of EEG-signal voltage differences (ΔV$_{EEG1}$, V$_{EEG2}$) can be used separately in each of the respective first and second hearing devices (HAD$_1$, HAD$_2$) (e.g. to control processing of an input audio signal) or combined in one of the hearing devices and/or in the auxiliary device (PRO, e.g. for display and/or further processing).

Figure 3:
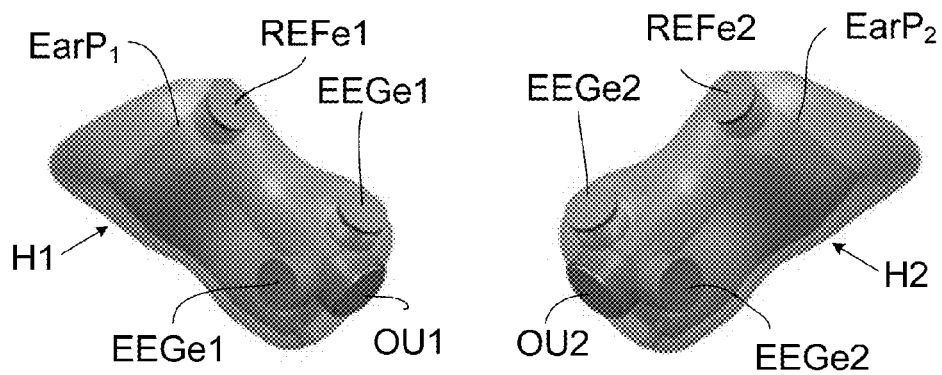
FIG. 3 shows exemplary first and second parts of a hearing assistance system according to the present disclosure, the first and second parts being form as ear moulds comprising EEG and reference electrodes, the ear moulds being adapted to fit into an ear canal of a user.

FIG. 3 shows exemplary first and second parts of a hearing assistance system according to the present disclosure, the first and second parts being formed as ear moulds ((ear)parts EarP$_1$, EarP$_2$, respectively) comprising EEG— (EEGe1, EEGe2) and reference—(REFe1, REFe2) electrodes, the ear moulds being adapted to fit into an ear canal of a user. Two EEG-electrodes and one reference-electrode are exemplarily shown. The first and second ear moulds comprise or constitute first and second housings (H1, H2), respectively, the first and second electrodes being located at or accessible from a surface of the first and second housings (H1, H2) to allow the first and second electrodes to contact the skin (SKIN) of the user in the ear or ear canal, when the first and second parts are operationally mounted at the respective ears of the user. FIG. 3 illustrates a practical embodiment of ear pieces (EarP$_1$, EarP$_2$) of the respective first and second hearing devices (HAD$_1$, HAD$_2$) of FIG. 2C. The ear pieces (EarP$_1$, EarP$_2$) may constitute the respective first and second parts (P1, P2), or the respective first and second hearing devices (HAD$_1$, HAD$_2$), or alternatively be in operational communication with other parts, e.g. first and second BTE-parts adapted for being located behind respective ears of the user. The BTE-parts may comprise some of the components for picking up, processing and presenting audio signals, e.g. one or more input transducers, a signal processing unit and one or more output transducers. The respective BTE parts and ear pieces may be connected via electrical conductors and/or wireless links. In the embodiment of FIG. 3, first and second output units (OU$_1$, OU$_2$) (e.g. loudspeakers, cf. e.g. SP units in FIG. 4) of the first and second hearing devices (HAD$_1$, HAD$_2$), respectively, are further schematically, indicated.

Figure 4:
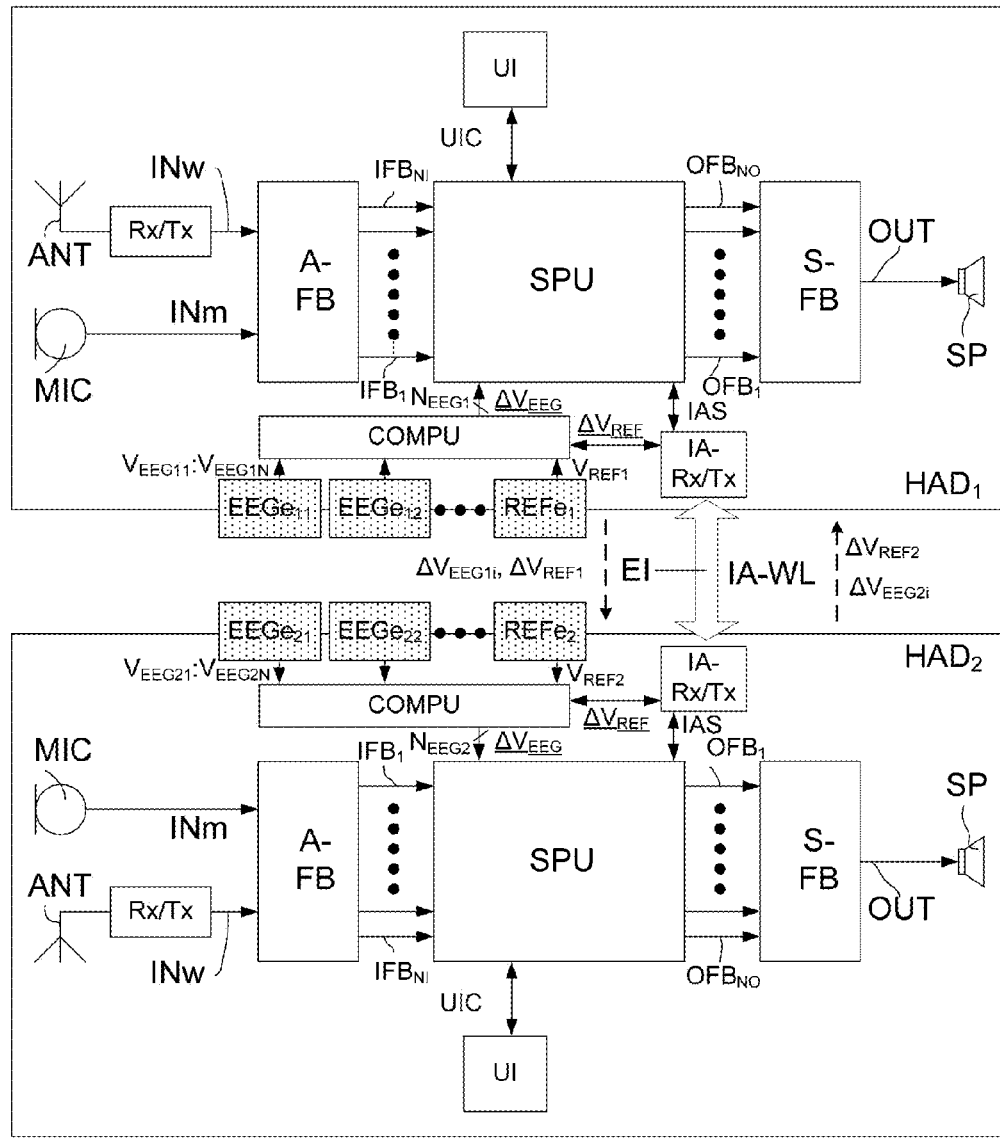
FIG. 4 shows an embodiment of a binaural hearing aid system comprising first and second hearing devices each comprising EEG and reference electrodes according to the present disclosure, FIG. 5 schematically shows electric field lines around a user's body when wearing a hearing assistance system comprising EEG electrodes according to the present disclosure (FIG. 5A) and an equivalent electric diagram for using the body to communicate a reference potential from one part of the hearing assistance system to the other (FIG. 5B)

FIG. 4 shows an embodiment of a binaural hearing aid system comprising first and second hearing devices (HAD$_1$, HAD$_2$), each comprising EEG and reference electrodes according to the present disclosure. The first and second hearing devices (HAD$_1$, HAD$_2$) are adapted for being located at or in left and right ears of a user. The hearing devices are adapted for exchanging information (including EEG signals, e.g. voltage reference signals ΔV$_{REF}$) between them via a wireless communication link (constituting the electric interface (EI) between the first and second parts of the hearing assistance system), e.g. a specific inter-aural (IA) wireless link (IA-WLS). The two hearing devices (HAD$_1$, HAD$_2$) are adapted to allow the exchange of status signals, e.g. including the transmission of reference voltages and/or EEG-signals generated by electrodes of one device at a particular ear to the device at the other ear. To establish the inter-aural link (IA-WLS), each hearing device comprises antenna and transceiver circuitry (here indicated by block IA-Rx/Tx). Each of the (e.g. substantially identical) hearing devices (HAD$_1$, HAD$_2$) of FIG. 4 may comprise the same functional components as described in connection with FIGS. 1 and 2.

Each of the hearing devices comprises a forward path for propagating a signal representing sound from an input unit (IU) to an output unit (OU), cf. e.g. FIG. 1. The forward path processes an input signal in the time-frequency domain. The input unit comprises a microphone (MIC) for converting an input sound to an electric input signal (INm). The input unit further comprises antenna and transceiver circuitry (ANT, Rx/Tx) for wirelessly receiving a direct electric input signal (INw) representing audio. The input unit further comprises an analysis filter bank (A-FB). The time domain input signals (INm, INw) are fed to the analysis filter bank (A-FB) for providing one of the input signals (INm, INw) or a weighted combination of the input signals (INm, INw) in a number NI of input frequency bands (cf. (time-variant) input band signals $IFB_1, \ldots, IFB_{NI}$). The input frequency bands may be processed individually in signal processing unit (SPU) providing a number NO of output frequency band signals $OFB_1, \ldots, OFB_{NO}$. The output unit comprises a synthesis filter bank (S-FB) and an output transducer. The output frequency band signals $OFB_1, \ldots, OFB_{NO}$ from the signal processing unit (SPU) are synthesized to a time domain output signal OUT in synthesis filter bank (S-FB). The resulting processed electric (time-domain) output signal OUT is fed to the output transducer, here loudspeaker (SP) for being presented to the user as an output sound.

Each of first and second hearing devices ($HAD_1$, $HAD_2$) comprises EEG and reference electrodes as described in connection with FIG. 2C. The EEG-voltages ($V_{EEG1i}$: $V_{EEG1N}$) and $V_{EEG21}$:$V_{EEG2N}$) and the reference voltages $V_{REF1}$ and $V_{REF2}$ ($\Delta V_{REF}$), respectively, are fed to the respective comparison units (COMPU) together with a reference voltage difference $\Delta V_{REF}$ received from the contralateral hearing device via the electric interface (EI), here inter-aural wireless link IA-WL. The number of EEG-signals of the first and second hearing devices ($HAD_1$, $HAD_2$) may be identical (N) or different ($N_{EEG1}$, $N_{EEG2}$) and will typically correspond to the respective number of EEG electrodes. The EEG-voltage difference signals $\Delta V_{EEG}$ are fed to the signal processing unit (SPU) for further processing and/or control of a signal processing algorithm in one or more frequency bands. Each of the first and second hearing devices ($HAD_1$, $HAD_2$) further comprises a user interface (UI) for influencing the function of the hearing assistance system and/or displaying information of relevance to the user, e.g. regarding the current analysis of the EEG-signals, cf. e.g. FIG. 6.

Figure 5A:
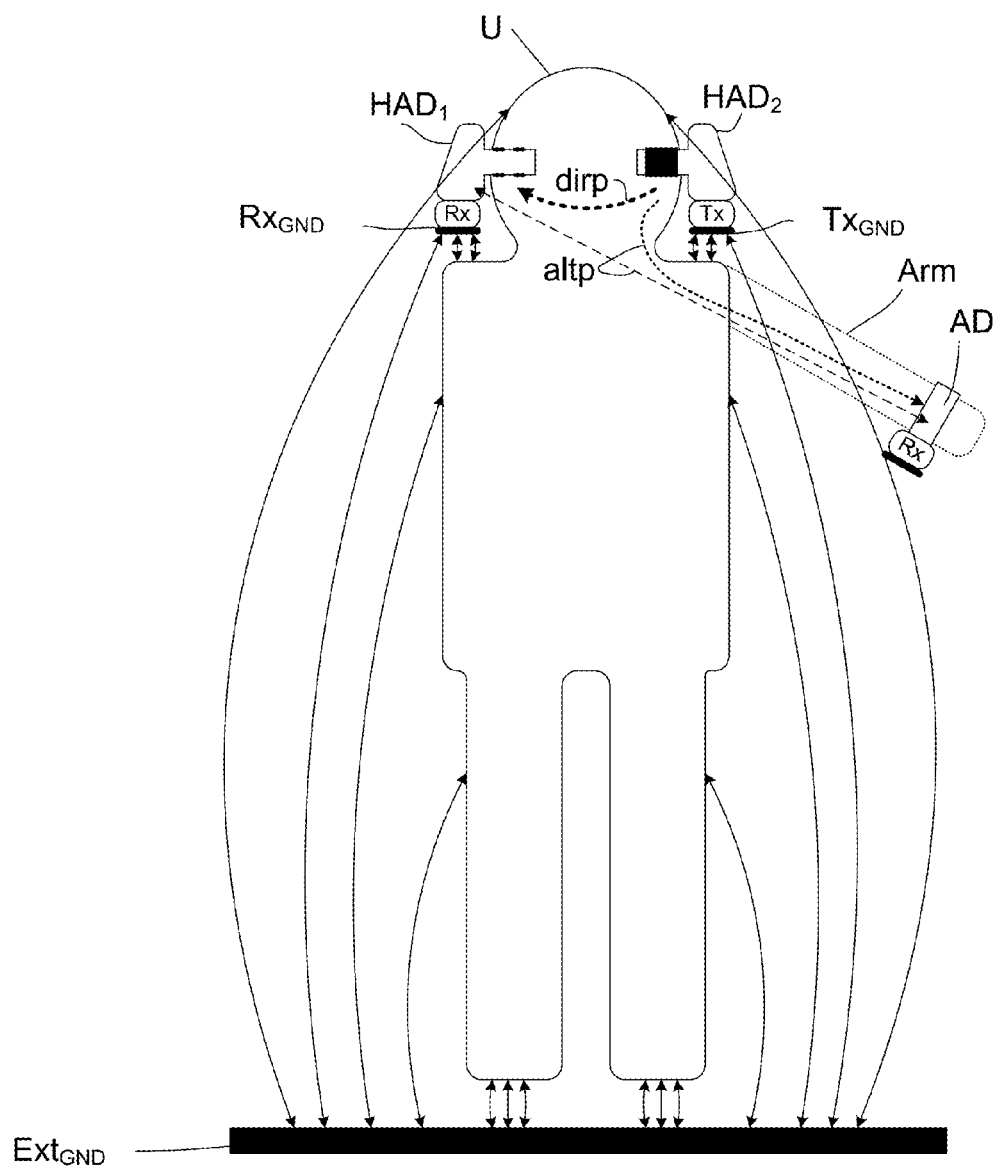
Figure 5B:
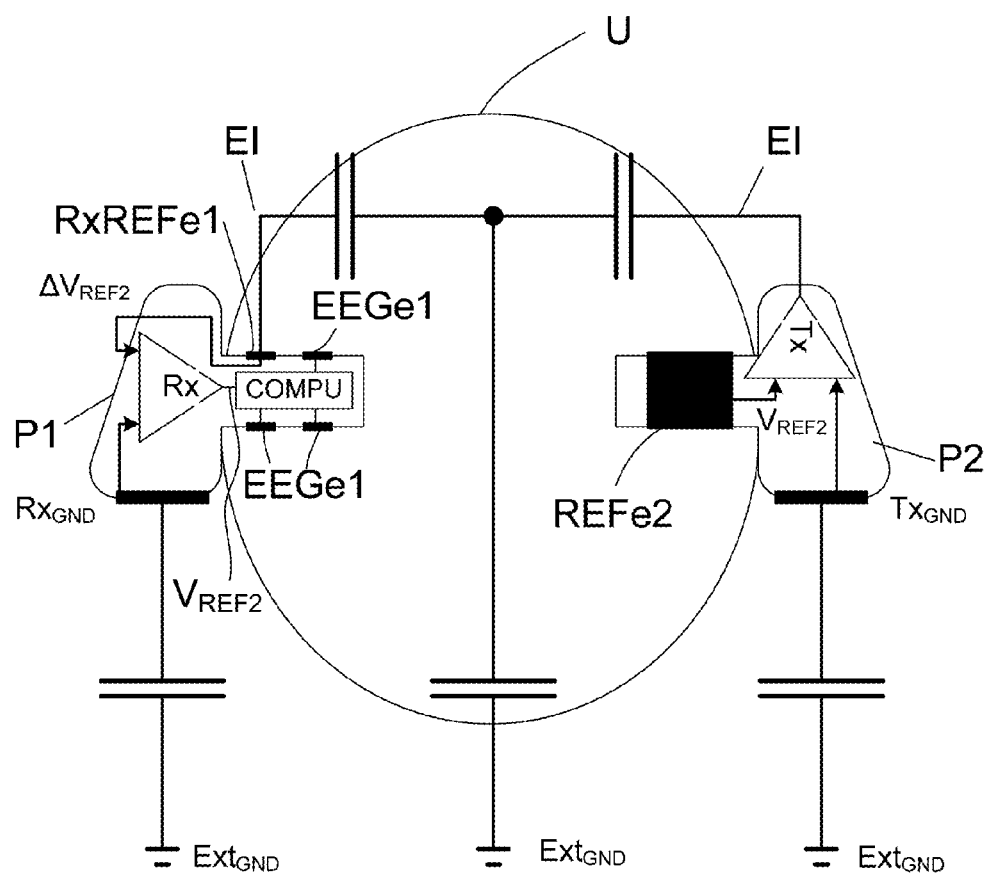

FIG. 5 schematically shows electric field lines around a user's (U) body when wearing a hearing assistance system comprising EEG-electrodes according to the present disclosure (FIG. 5A) and an equivalent electric diagram for using the body as transmission medium to communicate a reference potential from one part of the hearing assistance system to the other (FIG. 5B).

FIG. 5A illustrates the use of a hearing assistance system as discussed in connection with FIG. 2B. Each of the first and second hearing devices ($HAD_1$ comprising first part P1, $HAD_2$ comprising second part P2) comprises a separate ground electrode ($Rx_{GND}$ and $Tx_{GND}$, respectively) adapted to provide a virtual ground for reception/transmission of signals between the two devices. $Tx_{GND}$ is a virtual ground for transmitter (Tx) for transmitting a reference voltage picked up at the second hearing device ($HAD_2$) to the receiver (Rx) for receiving the reference voltage difference ($\Delta V_{REF2}$, in the form of reference voltage $V_{REF2}$ relative to virtual ground $Tx_{GND}$) in the first hearing device ($HAD_1$). One of the electrodes (RxREFe1) of first hearing device ($HAD_1$) is connected to the receiver (Rx) and used to receive the reference voltage difference $\Delta V_{REF2}$. The virtual Tx- and Rx-ground are substantially equal and established via the capacitive coupling to the external ground ($Ext_{GND}$) partly via the user's body.

FIG. 5B shows an equivalent model of the capacitive coupling of an electric signal from a transmitter (Tx) to a receiver (Rx) via a user's body. The comparison unit (COMPU) of the first hearing devices ($HAD_1$) comprising EEG-electrodes EEGe1 picks up EEG-voltages and receives reference voltage $V_{REF2}$ from the receiver Rx.

In an alternative embodiment (or additionally), the system further comprises a body-worn auxiliary device (AD in FIG. 5A), e.g. configured to be worn on an arm (Arm in FIG. 5A), e.g. the wrist. The body-worn auxiliary device comprises an electrode in contact with the skin of the user, and is adapted to receive a signal from one or both of the first and second hearing devices ($HAD_1$, $HAD_2$) by body communication (cf. receiver Rx and electrode on auxiliary device AD). In an embodiment, the reference voltage $V_{REF2}$ relative to virtual ground $Tx_{GND}$) is propagated from the second first hearing device ($HAD_2$) to the auxiliary device (AD) via body communication, and propagated from the auxiliary device to the first hearing device ($HAD_1$) either via body communication, or via a conventional wireless link (e.g. depending on the application or the link quality), cf. dotted and dashed arrows denoted altp in FIG. 5A. This solution may be provided as an alternative path to the direct path from the first ($HAD_1$) to the second ($HAD_2$) hearing device, cf. bold, dotted arrow, denoted dirp in FIG. 5A. The path from the second hearing device ($HAD_2$) to the auxiliary device (AD) positioned on the user's arm (Arm) in the same side as the ear where the second hearing device is positioned may (at certain conditions) prove more suited for body communication than the direct path (dirp) from the second to the first hearing device. In an embodiment, the provision of the reference voltage $V_{REF2}$ is provided by the second part to the first part with a view to minimizing the disturbance of the measured EEG-signals. In an embodiment, the measurements and/or transmission of the reference voltage $V_{REF2}$ are performed in particular time slots, e.g. repeatedly. In an embodiment, the EEG measurements are performed in time slots where the reference voltage $V_{REF2}$ is not transmitted.

U.S. Pat. No. 7,978,063 deals with a wireless network for monitoring a person including a physiological condition sensor, e.g. an electrocardiograph (ECG). The network comprises a relay system for communicating data from the sensor via the person's body using a near field capacitive body coupled communication technology.

Figure 6:
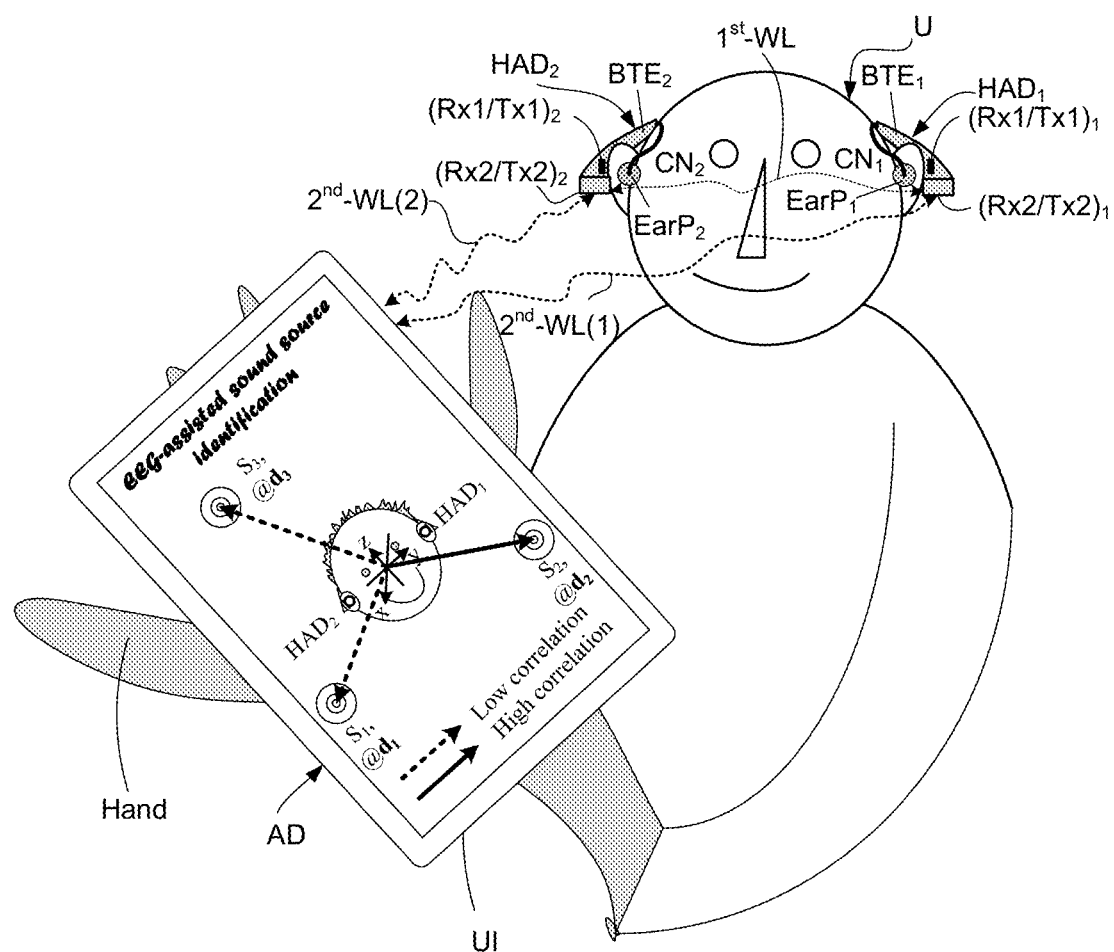
FIG. 6 shows an embodiment of a binaural hearing aid system according to the present disclosure comprising first and second hearing devices in communication with an auxiliary device functioning as a user interface for the binaural hearing aid system.

FIG. 6 shows an embodiment of a binaural hearing aid system according to the present disclosure comprising first and second hearing devices in communication with an auxiliary device functioning as a user interface for the binaural hearing aid system.

FIG. 6 shows an embodiment of a binaural hearing aid system comprising left (first) and right (second) hearing devices ($HAD_1$, $HAD_2$) in communication with a portable (handheld) auxiliary device (AD), e.g. a remote control or a SmartPhone, functioning as a user interface (UI) for the binaural hearing aid system. Each of the first and second hearing devices ($HAD_1$, $HAD_2$) comprises a BTE- and an ITE-part adapted for being located behind and in an ear, respectively of the user, and e.g. electrically connected via a connecting element ($CN_1$, $CN_2$ in FIG. 6). The first and second ITE-parts ($EarP_1$ and $EarP_2$, respectively, in FIG. 6) comprise EEG and reference electrodes as discussed in connection with FIG. 1 to FIG. 5. The first and second ITE-parts may further (each) e.g. comprise one or more input transducers, and an output transducer. In an embodiment, the BTE-parts (and the connecting elements) are dispensed with, so that all functionality of the hearing devices ($HAD_1$, $HAD_2$) is located in the respective ITE-parts ($EarP_1$, $EarP_2$). The first and second BTE-parts ($BTE_1$, $BTE_2$ in FIG. 6) may e.g. comprise a battery, one or more input transducers, a signal processing unit and wireless transceivers. In an embodiment, first and second BTE-parts (BTE$_1$, BTE$_2$) each comprise an output transducer and the attached first and second connecting elements (CN$_1$, CN$_2$) each comprise an acoustic conductor, e.g. e tube, for propagating sound from the output transducer of a BTE-part to the corresponding ITE-part (and thus to the ear drum of the ear in question). In an embodiment, the binaural hearing aid system comprises the auxiliary device (and the user interface) and is e.g. configured to display information related to the system, e.g. to the measurement and analysis of the EEG-signals, e.g. an estimate of a present cognitive state of the user, or an estimate of the location of an audio source that the user is most likely trying to listen to. The user interface displaying information of the binaural hearing aid system may be implemented as an APP of the auxiliary device (e.g. a SmartPhone). In the embodiment of FIG. 6, the available wireless links (constituting the electric interface EI) are denoted $1^{st}$-WL. (e.g. an inductive link between the hearing devices) and $2^{nd}$-WL(1) and $2^{nd}$-WL(2) (e.g. RF-links between the auxiliary device and the left and between the auxiliary device and the right hearing device, respectively). The $1^{st}$ and $2^{nd}$ wireless interfaces are implemented in the left and right hearing devices (HAD$_1$, HAD$_2$) by antenna and transceiver circuitry ((Rx1/Tx1)$_1$, (Rx2/Tx2)$_1$) and ((Rx1/Tx1)$_2$, (Rx2/Tx2)$_2$), respectively. The auxiliary device (AD) comprising the user interface (UI) is adapted for being held in a hand (Hand) of a user (U), and hence convenient for displaying information to the user and to be used by the user for controlling the system. The APP EEG-assisted sound source identification displays currently present sound sources (S$_1$, S$_2$, S$_3$) and their estimated localization (d$_1$, d$_2$, d$_3$) relative to the user (U). By correlating the captured EEG signals and the individual, currently present sound source signals (as e.g. provided by a source separation algorithm of the hearing device), sound sources having a correlation with the EEG signals below a predefined threshold value are denoted with low correlation' (dotted arrow, here sources S$_1$, S$_3$) and sound sources having a correlation with the EEG signals above a predefined threshold value are denoted with 'High correlation' (full line arrow, here source S$_2$). Such information may be used to automatically and/or manually bring beamformers of the first and second hearing devices (HAD$_1$, HAD$_2$) to focus on the sound source (S$_2$) having the relatively higher correlation with the EEG signals. Thereby an improved perception (e.g. intelligibility of speech) of sound in a multi-sound source environment may be provided. The (automatic) correlation of brainwave signals and current sound source signals is e.g. dealt with in US2014098981A1. US2014098981A1 deals with a hearing device comprising a sensor for measuring brainwaves of the user of the hearing device and which adapts its audio processing in dependence on the measured brainwaves, in particular of the coherence between the measured brainwaves and an audio signal picked up by and processed by a forward path of the hearing device. A manual selection of the sound source (e.g. S$_2$) currently having the relatively higher correlation with the (current EEG-signals) may e.g. be performed via the user interface (UI), e.g. by touching the source in question (e.g. S$_2$) on the display. The calculations of correlation between audio sources and brainwave signals may e.g. be performed in the respective hearing devices and the results transmitted to the auxiliary device for comparison (evaluation) and display. Alternatively, the calculations may be performed in the auxiliary device to save power in the hearing devices.

Figure 7A:
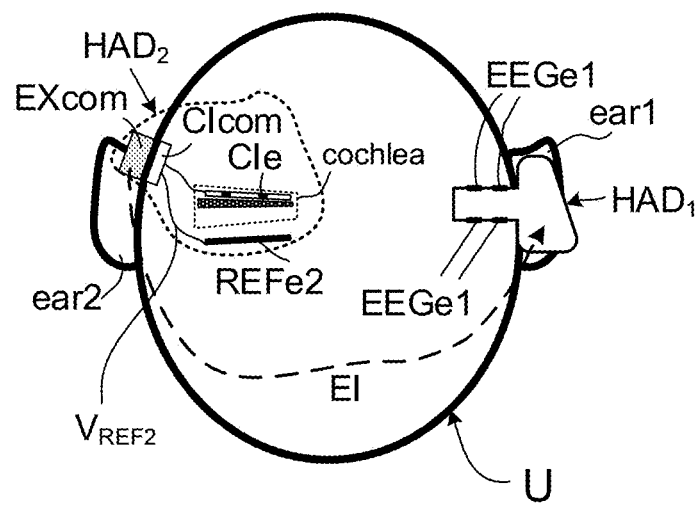
FIG. 7 shows two different configurations (FIG. 7A, 7B) of a hearing assistance system according to the present disclosure.
Figure 7B:
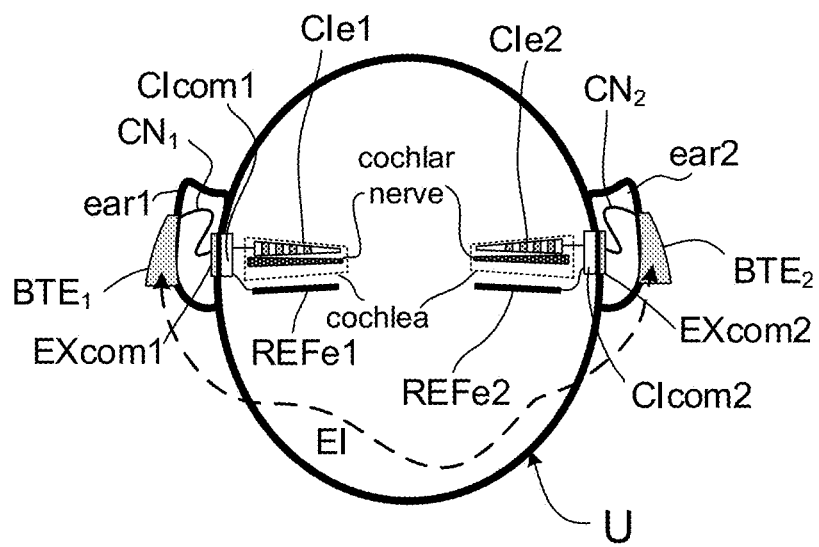

FIG. 7 shows two different configurations (FIG. 7A, 7B) of a hearing assistance system according to the present disclosure.

In an aspect, at least one of the electrodes of the hearing assistance system is fully or partially implanted in the head of the user. In an embodiment the first part may be adapted for being partially implanted in the head (e.g. in or near cochlea) at a first (and/or second) ear of a user. In an embodiment, an implanted electrode is used as a reference electrode for referencing low-voltage electric signal from the user's brain to provide the brainwave voltage difference signals (cf. FIG. 7A). In an embodiment, an implanted electrode is used to pick up a low-voltage electric signal from the user's brain (cf. FIG. 7B).

FIG. 7A illustrates a hearing assistance system comprising a first hearing assistance device (HAD$_1$) located at a first ear (ear1) of a user (U) and comprising a number of first electrodes (EEGe1), e.g. three or four, located at a surface of a first housing to allow the first electrodes to contact the skin of the user when the first hearing assistance device is operationally mounted on the user. At least some of the first electrodes (EEGe1, and possibly the first hearing assistance device) are adapted to pick up a low-voltage electric signal from the user's brain. The first hearing assistance device may e.g. be a bone anchored type or an air conduction type hearing assistance device providing an output stimulus configured to be perceived by the user as an auditory signal (sound). The hearing assistance system further comprises a second hearing assistance device (HAD$_2$) located at a second ear (ear2) and comprising reference electrode (RFEe2) implanted into the user's head at a second ear (ear2). The reference electrode is in the embodiment of the FIG. 7A located near but outside cochlea (and may e.g. additionally form a reference electrode of a multichannel cochlear implant electrode (CIe) implanted into the users cochlea (cochlea, as indicated in FIG. 7A)). The second hearing assistance device (HAD$_2$) (indicated by the bold dotted enclosure) comprises an external part (EXcom) as well as the implanted part (REFe2, CIe, CIcom). The implanted part comprises communication unit (CIcom) adapted to transmit reference voltage $V_{REF2}$ to external communication unit EXcom. The hearing assistance system comprises an electrical interface (EI) as discussed in connection with previous drawings (FIG. 1 to FIG. 5). The reference voltage $V_{REF2}$ may be communicated to the first hearing assistance device (HAD$_1$) by any of the methods discussed in connection with FIG. 1 to FIG. 5.

FIG. 7B illustrates a hearing assistance system comprising first and second hearing assistance devices (HAD$_1$, HAD$_2$) of the cochlear implant type. Each of the first and second hearing assistance devices comprises an implanted part comprising a reference electrode (REFe1, REFe2, respectively) located (e.g. near, but) outside cochlea and a multichannel cochlear implant electrode (CIe1, CIe2) implanted into (or near) the users cochlea (cochlea). The multichannel cochlear implant electrodes are configured to (electrically) stimulate the cochlear nerve of the user (and optionally for capturing evoked potentials (ECAPs) resulting from nerve stimulation). Each of the first and second hearing assistance devices comprises further comprises an implanted communication unit (CIcom1, CIcom2, respectively) adapted to transmit the respective reference voltage ($V_{REF1}$, $V_{REF2}$) to an external communication unit (EXcom1, EXcom2, respectively) adapted for receiving the reference voltage in question. The external communication units are electrically connected to respective BTE-parts (BTE$_1$, BTE$_2$), here via electric cable (CN$_1$, CN$_2$). The BTE parts (BTE$_1$, BTE$_2$) may e.g. comprise processing units, input transducer(s), wireless transceivers, etc. The implanted and external communication units (CIcom1, CIcom2, and EXcom1, EXcom2, respectively) may further implement a link for transferring electric stimuli (or coded electric stimuli) from the BTE-part to the implanted part to be applied to (at least some of) the respective cochlear implant electrodes. Likewise, evoked potentials, e.g. brainwave signals, may be transferred from the implanted part to the BTE-part for further processing via the link provided by the implanted and external communication units. In an embodiment, the multichannel cochlear implant electrodes (CIe1, CIe2) are used to record brainwave signals and the respective reference electrode (REFe1, REFe2) are used as reference potentials for the corresponding brainwave signals (to provide respective brainwave voltage difference signals in the first and second hearing assistance devices. In an embodiment, the reference potentials $V_{REEF1}$ and $V_{REEF2}$ picked up by the first and second reference electrodes (REFe1, REFe2, respectively) are exchanged between the two hearing assistance devices ($HAD_1$, $HAD_2$). In an embodiment, the first reference potential $V_{REEF1}$ picked up by the first reference electrode REFe1 is used as a reference voltage for the brainwave signals picked up by the second multichannel cochlear implant electrode (CIe2) and vice versa. This may have the advantage of proving larger brainwave voltage differences. The reference voltages $V_{REF1}$ and $V_{REF2}$ may be communicated to the second and first hearing assistance devices ($HAD_2$ and $HAD_1$), respectively, via the electrical interface (EI) by any of the methods discussed in connection with FIG. 1 to FIG. 5.

The brainwave voltage differences may e.g. provide information about the current state of the user or which audio source the user is currently focusing on, etc., and may be used to influence the stimulation of the electrodes of the multi-electrode arrays (CI1 and CI2, respectively) to provide an improved perception by the user of an audio signal picked up or received by the hearing assistance system.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof.

REFERENCES

US2014098981A1 (OTICON) 10 Apr. 2014
U.S. Pat. No. 7,206,423 (UNIV. ILLINOIS) 17 Apr. 2007
U.S. Pat. No. 7,978,063 (PHILIPS) 17 Sep. 2009
[Zimmerman; 1996], T. G. Zimmerman, *Personal Area Networks: Near-field intrabody communication*, IBM SYSTEMS JOURNAL, VOL. 35, NO. 3&4, 1996.
[Cho et al.; 2007] Cho N., Yoo J., Song S. J Lee J., Jeon S., Yoo H. J., *The Human Body Characteristics as a Signal Transmission Medium for Intrabody Communication*, IEEE TRANSACTIONS ON MICROWAVE THEORY AND TECHNIQUES, VOL. 55, NO. 5, MAY 2007
[Lucev et al.; 2011] Lucev Z., Krois I., Cifrek M., *A capacitive intrabody communication channel from 100 kHz to 100 MHz*, Instrumentation and Measurement Technology Conference (I2MTC), 2011 IEEE.

The invention claimed is:

1. A hearing assistance system comprising:
a first part adapted for being mounted fully or partially at a first ear or in an ear canal of the first ear of a user, the first part including:
a first housing, and
a number of first electrodes located at a surface of said first housing to allow said first electrodes to contact the skin of the user when said first part is operationally mounted on the user, each of the first electrodes being adapted to pick up a low-voltage electric signal from the user's brain;
a second part adapted for being mounted on the body spatially separated from said first part, the second part including:
a number of second electrodes arranged to allow said second electrodes to contact the skin of the user when second said part is operationally mounted on the user, and
at least one of the second electrodes of the second part being configured as a reference electrode and adapted to pick up a reference voltage intended to constitute a reference voltage for the low-voltage electric signal(s) from the user's brain picked up by the first electrodes thereby allowing a voltage difference signal to be determined for each of said first electrodes;
a comparison unit for determining said voltage difference signal(s); and
an electric interface allowing said reference voltage or a measure representative thereof to be transferred from said second part to said comparison unit.

2. A hearing assistance system according to claim 1 wherein the electric interface comprises a galvanic connection.

3. A hearing assistance system according to claim 1 wherein the electric interface comprises a wireless link.

4. A hearing assistance system according to claim 3 wherein the wireless link is based on radiated fields or on near-field coupling.

5. A hearing assistance system according to claim 1 wherein the electric interface comprises a body-network.

6. A hearing assistance system comprising:
a first part adapted for being mounted fully or partially at a first ear or in an ear canal of the first ear of a user, the first part including:
a first housing, and
a number of first electrodes located at a surface of said first housing to allow said first electrodes to contact the skin of the user when said first part is operationally mounted on the user, each of the first electrodes being adapted to pick up a low-voltage electric signal from the user's brain; and
a second part adapted for mounting on the body spatially separated from said first part, the second part including:
a number of second electrodes arranged to allow said second electrodes to contact the skin of the user when second said part is operationally mounted on the user, and
at least one of the second electrodes of the second part being configured as a reference electrode and adapted to pick up a reference voltage intended to constitute a reference voltage for the low-voltage electric signal(s) from the user's brain picked up by the first electrodes thereby allowing a voltage difference signal to be determined for each of said first electrodes,
wherein
the hearing assistance system comprises a comparison unit for determining said voltage difference signal(s), and an electric interface allowing said reference voltage or a measure representative thereof to be transferred from said second part to said comparison unit,
in the electric interface comprises a body-network, and each of the first and second parts of the hearing assistance system comprises one of a Tx- and Rx-ground electrode exhibiting substantially equal virtual Tx- and Rx-ground potentials established via a capacitive coupling to an external ground, at least partly via the user's body.

7. A hearing assistance system according to claim 1 comprising a hearing aid, a headset, an earphone, an ear protection device or a combination thereof.

8. A hearing assistance system according to claim 1 the hearing assistance system is configured to maximize the area of contact of the reference electrode with the skin.

9. A hearing assistance system according to claim 1 wherein the first part is implemented as an ear piece adapted for being located in or at one of the left or right ear or ear canals of the user.

10. A hearing assistance system according to claim 1 wherein
the first comprises a number of first EEG electrodes and a first reference electrode, and
the second part includes a number of second EEG electrodes and a second reference electrode.

11. A hearing assistance system according to claim 1 wherein the first part comprises the comparison unit.

12. A hearing assistance system according to claim 1 wherein the first and second parts form part of first and second hearing devices, e.g. first and second hearing aids.

13. A hearing assistance system according to claim 12, further comprising an auxiliary device, and wherein the system is adapted to establish a communication link between the hearing device(s) and the auxiliary device to provide that information can be exchanged between them, or forwarded from one to the other.

14. A hearing assistance system according to claim 13 wherein the auxiliary device comprises a SmartPhone configured to provide the function of a user interface of the hearing device.

15. Use of a hearing assistance system according to claim 1.

16. A hearing assistance system comprising:
a first part including a first hearing aid adapted for mounting fully or partially at a first ear or in an ear canal of the first ear of a user, the first hearing aid including:
a first housing, and
a number of first electrodes located at a surface of said first housing to allow said first electrodes to contact the skin of the user when said first part is operationally mounted on the user, each of the first electrodes being adapted to pick up a low-voltage electric signal from the user's brain;
a second part adapted for being mounted on the body spatially separated from said first part, the second part including:
a number of second electrodes arranged to allow said second electrodes to contact the skin of the user when second said part is operationally mounted on the user, and
at least one of the second electrodes of the second part being configured as a reference electrode and adapted to pick up a reference voltage intended to constitute a reference voltage for the low-voltage electric signal(s) from the user's brain picked up by the first electrodes;
a comparison unit for determining and/or processing voltage difference signal(s); and
an electric interface allowing said reference voltage or a measure representative thereof to be transferred from said second part to said comparison unit, thereby allowing a voltage difference signal to be determined and/or processed for each of said first electrodes.

17. A hearing assistance system according to claim 16 wherein the electric interface comprises a body-network.

18. A hearing assistance system comprising:
a first part including a first hearing aid adapted for mounting fully or partially at a first ear or in an ear canal of the first ear of a user, the first part including:
a first housing, and
a number of first electrodes located at a surface of said first housing allowing said first electrodes to contact the skin of the user when said first part is operationally mounted on the user, each of the first electrodes being adapted to pick up a low-voltage electric signal from the user's brain;
a second part adapted for mounting on the body spatially separated from said first part, the second part including:
a number of second electrodes arranged to allow said second electrodes to contact the skin of the user when second said part is operationally mounted on the user, and
at least one of the second electrodes of the second part being configured as a reference electrode and adapted to pick up a reference voltage intended to constitute a reference voltage for the low-voltage electric signal(s) from the user's brain picked up by the first electrodes;
a comparison unit for determining and/or processing voltage difference signal(s); and
an electric interface allowing said reference voltage or a measure representative thereof to be transferred from said second part to said comparison unit, thereby allowing a voltage difference signal to be determined and/or processed for each of said first electrodes, wherein
in the electric interface comprises a body-network, and each of the first and second parts of the hearing assistance system comprises one of a Tx- and Rx-ground electrode exhibiting substantially equal virtual Tx- and Rx-ground potentials established via a capacitive coupling to an external ground, at least partly via the user's body.

19. A hearing assistance system according to claim 16 wherein the first and second parts form part of first and second hearing devices, e.g. first and second hearing aids.

20. A hearing assistance system according to claim 16 wherein the first and/or second part comprises an analogue to digital converter to digitize and possibly amplify said voltage difference signals.

* * * * *